United States Patent [19]

Ariki et al.

[11] 4,351,976

[45] Sep. 28, 1982

[54] METHOD FOR PURIFYING 1,2-DICHLOROETHANE

[75] Inventors: Yusaku Ariki; Takio Hino; Noboru Yoshida, all of Takasago, Japan

[73] Assignee: Kanegafuchi Kagaku Kogyo Kabushiki Kaisha, Osaka, Japan

[21] Appl. No.: 246,154

[22] Filed: Mar. 23, 1981

[30] Foreign Application Priority Data

Mar. 26, 1980 [JP] Japan ................. 55-39591

[51] Int. Cl.$^3$ .............................................. B01D 3/34
[52] U.S. Cl. ..................................... 570/262; 203/51; 203/67
[58] Field of Search ...................... 203/67, 71, 68, 70; 570/262, 243, 246, 252

[56] References Cited

PUBLICATIONS

"Vinyl Chloride"; Hydrocarbon Processing; Nov. 1975; pp. 214–217.

Primary Examiner—Frank Sever

Attorney, Agent, or Firm—Armstrong, Nikaido, Marmelstein & Kubovcik

[57] ABSTRACT

An improvement of a method for purifying 1,2-dichloroethane by passing through a distillation column a crude 1,2-dichloroethane produced by oxychlorination of ethylene with at least one of a crude 1,2-dichloroethane produced by direct chlorination of ethylene and a crude uncracked 1,2-dichloroethane recovered in thermal cracking of 1,2-dichloroethane, the improvement which comprises feeding the oxychlorination-produced 1,2-dichloroethane to an upper plate of the distillation column than a plate of the column to which at least one of the direct chlorination-produced 1,2-dichloroethane and the uncracked 1,2-dichloroethane is fed, and recovering 1,2-dichloroethane as a bottom product. The purification method is very useful in the production of vinyl chloride by thermal cracking of 1,2-dichloroethane, since carbon tetrachloride effective as a thermal cracking catalyst is stably recovered in high concentrations with 1,2-dichloroethane, while removing other low boiling impurities, and the method is economically practiced.

4 Claims, 2 Drawing Figures

METHOD FOR PURIFYING 1,2-DICHLOROETHANE

BACKGROUND OF THE INVENTION

The present invention relates to the purification of 1,2-dichloroethane (ethylene dichloride), and more particularly to an improvement of a method for purifying crude 1,2-dichloroethane by employing a distillation column of plate type or packed type.

At the present day, vinyl chloride has been in general prepared industrially by a process in which purified 1,2-dichloroethane is thermally cracked. Crude 1,2-dichloroethane produced by oxychlorination of ethylene (hereinafter referred to as "oxy-EDC"), crude 1,2-dichloroethane produced by direct chlorination of ethylene (hereinafter referred to as "direct-EDC") and uncracked 1,2-dichloraethane (hereinafter referred to as "uncracked-EDC") recovered in the thermal cracking of 1,2-dichloroethane are purified and employed as a feed 1,2-dichloroethane in the production of vinyl chloride by an oxychlorination process.

The crude oxy-EDC usually contains as impurities low-boiling compounds (having a boiling point of not more than 83.7° C./760 mmHg) such as ethyl chloride, cis-dichloroethylene, chloral, carbon tetrachloride and trichloroethylene and high-boiling compounds (having a boiling point of not less than 83.7° C./760 mmHg) such as 1,1,2-trichloroethane and tetrachloroethane. On the other hand, the crude direct-EDC usually contains as impurities low-boiling compounds such as ethyl chloride, 1,1-dichloroethane and chloroform and high-boiling compounds such as 1,1,2-trichloroethane and tetrachloroethane. Also, the uncracked-EDC usually contains as impurities low-boiling compounds such as ethyl chloride, chloroprene and chloroform and high-boiling compounds such as monochlorobenzene.

A distillation column has been employed for purifying these crude 1,2-dichloroethanes of three kinds to the extent such that 1,2-dichloroethane (hereinafter referred to as "EDC") can be cracked without any problems to produce vinyl chloride of usual quality. FIG. 1 is a flow sheet showing a conventional purification method using a distillation column. In general, the purification is carried out by passing the crude EDC first through a so-called low boiler column I for removing impurities having lower boiling points than EDC and then through a high boiler column II for removing impurities having higher boiling points than EDC. In a conventional purification method, in order to remove the low-boiling compounds, the above-mentioned crude EDC of three kinds are usually mixed at an appropriate place in an appropriate manner and are fed through a feed pipe 1 to a certain appropriate one plate of the low boiler column I, and low-boiling compounds are distilled from the top of the column through a pipe 3. The bottom product is then fed through a pipe 4 to the high boiler column II, and the purified EDC is recovered from the top of the column through a pipe 5, while high-boiling impurities are removed from the bottom of the column through a pipe 6. In the low boiler column I, it is necessary to purify the crude EDC so that EDC recovered as a bottom product from the bottom of the column contains no low-boiling compounds, or even if contains, the amount of low-boiling compounds is so small that they do not hinder the thermal cracking of EDC in the production of vinyl chloride, in other words, do not decrease the thermal cracking rate and also do not cause clogging of a reaction tube, e.g. less than several hundreds p.p.m. When carbon tetrachloride included in the crude oxy-EDC, which is effective as a catalyst for thermal cracking of EDC, is recovered as a bottom product together with EDC, it is possible to conduct the thermal cracking of EDC at a relatively low temperature, since the purified EDC contains the carbon tetrachloride catalyst.

However, in a conventional distillation method as mentioned above in which the mixed crude EDC is fed to a certain one plate of a distillation column, the attempt of including carbon tetrachloride into the purified EDC without increasing the feed amount of steam has accompanied the defect that the concentration of other low-boiling compounds in the purified EDC also increases. On the other hand, when it is attempted to decrease the concentration of low-boiling compounds, carbon tetrachloride is also distilled away together with other low-boiling compounds. Further, when the amount of supplied steam is increased in order to raise the concentration of carbon tetrachloride in the purified EDC with keeping the concentration of other low-boiling compounds low, not only the utility cost increases, but also the concentration of carbon tetrachloride largely changes by a slight change in the conditions of operating a low boiler column, so upon preparing vinyl chloride by thermal cracking of the thus purified EDC, the conversion is not stabilized.

Accordingly, it is an object of the present invention to provide an improved method for purifying the crude oxy-EDC, crude direct-EDC and uncracked-EDC by employing a distillation column, which results in great effectiveness in steam saving.

A further object of the invention is to provide an improved method of purifying crude EDC by which in one distillation column for removing low-boiling impurities, purified EDC containing carbon tetrachloride in increased concentrations can be recovered as a bottom product, while other low-boiling impurities are removed from the top of the column.

These and other objects of the present invention will become apparent from the description hereinafter.

SUMMARY OF THE INVENTION

In accordance with the present invention, there is provided an improvement of a method for purifying 1,2-dichloroethane by passing through a distillation column a crude 1,2-dichloroethane produced by oxychlorination of ethylene with at least one of a crude 1,2-dichloroethane produced by direct chlorination of ethylene and a crude uncracked 1,2-dichloroethane recovered in thermal cracking of 1,2-dichloroethane, the improvement which comprises feeding a crude 1,2-dichloroethane produced by the oxychlorination to an upper plate of a distillation column than a plate of the column to which at least one of a crude 1,2-dichloroethane produced by the direct chlorination and a crude uncracked 1,2-dichloroethane recovered in the thermal cracking is fed, and recovering 1,2-dichloroethane as a bottom product.

DETAILED DESCRIPTION

According to the method of the present invention, by feeding crude EDC to two appropriate plates of a low boiler column, a low-boiling compounds can be removed as a distillate with a far less amount of steam supplied than that required in a conventional method in which crude EDC is fed to one plate of a low boiler column. Also, carbon tetrachloride which is useful as a catalyst of thermal cracking of EDC, can be accumulated in EDC subjected to the cracking reaction more easily in higher concentration and economically as compared with a conventional feeding method, since carbon tetrachloride included in feed materials can be recovered with EDC as a bottom product, and thereafter recycled and fed to the lower plate of a low boiler column. It is possible to increase the concentration of carbon tetrachloride to 1,000 to 5,000 p.p.m., especially 3,000 to 5,000 p.p.m., and if desired, to more than 5,000 p.p.m., with keeping the concentration of low-boiling compounds low, and moreover to maintain this effect stably. Further, the amount of steam supplied to the distillation column can be decreased to about ⅓ time that required in a conventional method.

In the present invention, a known column such as a plate column or a packed column can be employed as a distillation column.

Figure 1:
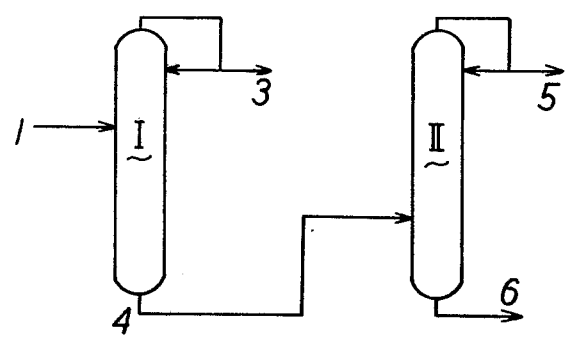
FIG. 1 is a flow sheet illustrating a conventional distillation system by one plate EDC feeding.
Figure 2:
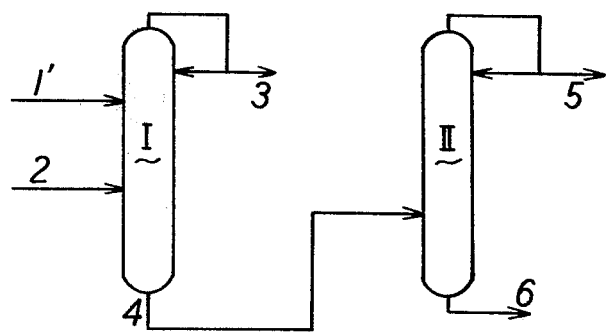
FIG. 2 is a flow sheet illustrating a distillation system according to the present invention by multi-plate EDC feeding.

An embodiment of the purification method of the present invention is explained in detail below with reference to FIG. 2.

A crude oxy-EDC containing carbon tetrachloride is fed through a pipe 1' to a plate positioned slightly lower than the top of a distillation column I for removal of low-boiling compounds, and simultaneously at least one of direct-EDC and an uncracked-EDC is fed through a pipe 2 to a lower plate of the column I than the oxy-EDC feed plate. It is preferable to employ as a feed material the uncracked-EDC recovered in the production of vinyl chloride by thermal cracking of EDC, since the concentration of carbon tetrachloride in the obtained purified EDC can be readily increased to a desired concentration.

In the early stage of the operation, even if a large portion of carbon tetrachloride included in the oxy-EDC is recovered in the purified EDC, its concentration is relatively low, since the uncracked-EDC contains scarcely carbon tetrachloride. However, since carbon tetrachloride made once to include in the purified EDC remains almost in the uncracked-EDC in the thermal cracking step of EDC for the production of vinyl chloride and is fed again to the low boiler column I in a circulating manner, the concentration of carbon tetrachloride in the obtained purified EDC is gradually increased. Therefore, it is possible to increase the concentration of carbon tetrachloride to a desired concentration without adding carbon tetrachloride from the outside. The concentration of carbon tetrachloride in the uncracked-EDC at that time is higher than that in the oxy-EDC. Thus, upon recovering carbon tetrachloride, it is efficient to make the recovery percentage from the uncracked-EDC containing carbon tetrachloride in high concentrations higher than the recovery percentage from the oxy-EDC containing carbon tetrachloride in relatively low concentrations, and this is also important in viewpoint of stable recovery. Also, it is a key point for efficiently removing low-boiling compounds to make the removal percentage of low-boiling compounds from the oxy-EDC containing them in high concentrations higher than the removal percentage of low-boiling compounds from the uncracked-EDC and direct-EDC containing them in low concentrations.

The recovery percentage of carbon tetrachloride and the removal percentage of low-boiling compounds are determined by the ratio of the amount of a falling liquid to the amount of a rising gas within the column. According to the method of the present invention, it is possible to raise the ratio of gas to liquid and thus to raise the removal percentage of low-boiling compounds by feeding the oxy-EDC to an upper plate of the column, and it is possible to lower the ratio of gas to liquid and thus to raise the recovery percentage of carbon tetrachloride by feeding the direct-EDC and/or the uncracked-EDC to a lower plate of the column. In order to effectively practice the present invention, it is desirable that the number of the plates between the upper plate to be fed with the oxy-EDC and the lower plates to be fed with the direct-EDC and/or the uncracked-EDC, the number of the plates between the top of the column and the upper plate and the number of the plates between the lower plate and the bottom of the column are at least 10 plates, respectively, but is not critical.

Also, in order to effectively practice the present invention, it is desirable to feed the whole amount of the oxy-EDC, the whole amount of the uncracked-EDC and the whole amount of the direct-EDC which are produced or recovered in a vinyl chloride manufacturing plant by an oxychlorination process, to the upper portion, the middle portion and the lower portion of the distillation column, respectively. However, in the practical operation, it is not necessary to define the column into three portions and to completely separately feed the crude EDC of three kinds. The saving of steam and the inclusion of carbon tetrachloride into the purified EDC can be easily attained by feeding the crude oxy-EDC to an upper plate of a distillation column than a plate of the column to which other crude EDC, i.e. at least one of the direct-EDC and the uncracked-EDC. The crude oxy-EDC to be fed to the upper plate of the column may be the oxy-EDC alone or a mixture of oxy-EDC as a main component with other crude EDC, i.e. direct-EDC and/or uncracked-EDC. The other crude EDC to be fed to the lower plate of the column than the upper oxy-EDC feed plate may be the direct-EDC alone, the uncracked-EDC alone, a mixture of the direct-EDC and the uncracked-EDC or a mixture of at least one of the direct-EDC and the uncracked-EDC as a main component with the oxy-EDC. In the above-mentioned cases, the ratio of the oxy-EDC contained in the total EDC fed to the upper plate always has to be higher than the ratio of the oxy-EDC contained in the total EDC fed to the lower plate.

In a vinyl chloride manufacturing plant according to a usual balanced process, the proportion of the oxy-EDC, uncracked-EDC and direct-EDC is about 1:2:1 when the conversion of the purified EDC is kept 50%.

When the method of the present invention is most efficiently practiced, the amount of steam supplied to the low boiler column can be reduced to about ⅓ time that required in a conventional method. In addition to such a large energy saving, it is also possible to suitably control the concentration of carbon tetrachloride in the purified EDC obtained through a high boiler column within the range of 1,000 to 5,000 p.p.m. Further, if necessary, it is possible to increase the concentration to more than 5,000 p.p.m. The concentration control can be conducted by adjustment of the concentration of low-boiling compounds in the liquid at the top of the low boiler column, and the temperature of a suitable specific plate at the concentrating portion of the column is usually used as a substitution characteristic for this purpose. Thus, by controlling the temperature of the concentrating portion of the column, carbon tetrachloride can be easily recovered with purified EDC as a bottom product in a desired concentration, while removing other compounds having a lower boiling point than that of carbon tetrachloride as a distillate from the top of the column.

Also, according to the present invention, it is possible to decrease the sectional area of a distillation column and the heat transfer areas of a cooler and a reboiler to ⅓ time those in a conventional method and, therefore, the construction cost can be cut down. The economical efficiency of the present invention is scarcely influenced by the construction cost of EDC feeding equipment newly installed for practicing the present invention. Thus, the present invention not only provides an economical method for the purification of EDC, but also has the advantages of the reduction of the construction cost, easiness of the operation and easiness of the industrialization.

The method of the present invention is more specifically described and explained by means of the following Examples and Comparative Example, in which all % and p.p.m. are by mole unless otherwise noted.

COMPARATIVE EXAMPLE

To the 60th plate from the bottom of a low boiler distillation column consisting of 75 plates were fed 15 tons/hour of a crude oxy-EDC of 96.3% in purity containing 840 p.p.m. of carbon tetrachloride obtained by oxychlorination of ethylene, 15 tons/hour of a crude direct-EDC of 99.5% in purity containing 30 p.p.m. of carbon tetrachloride obtained by direct chlorination of ethylene and 30 tons/hour of uncracked-EDC of 99.8% in purity containing 750 p.p.m. of carbon tetrachloride. The amount of a liquid taken out from the top of the column was adjusted so that the temperature of the 70th plate was maintained at 120° C., and steam was supplied to a reboiler located at the bottom of the column in an amount of 12.8 tons/hour. The purified EDC recovered from the column bottom contained 350 p.p.m. of carbon tetrachloride and 170 p.p.m. in total of other low-boiling compounds.

In order to further increase the concentration of carbon tetrachloride, the steam supplied to the reboiler was increased to 15.5 tons/hour and the temperature of the 70th plate was lowered by 8° C. The purified EDC obtained from the column bottom after 6 hours from the above operation contained 3,000 p.p.m. of carbon tetrachloride, but the concentration of carbon tetrachloride was not stabilized and varied within the range of 1,600 to 4,100 p.p.m. The maximum concentration of other low-boiling compounds in the purified EDC during this operation was 200 p.p.m.

EXAMPLE 1

According to the method of the present invention, 15 tons/hour of a crude oxy-EDC of 96.3% in purity containing 840 p.p.m. of carbon tetrachloride was fed to the 60th plate from the bottom of a low boiler distillation column consisting of 75 plates, and 15 tons/hour of a crude direct-EDC of 99.5% in purity containing 30 p.p.m. of carbon tetrachloride and 30 tons/hour of uncracked-EDC of 99.8% in purity containing 750 p.p.m. of carbon tetrachloride were fed to the 30th plate from the bottom of the column. Steam was supplied to a reboiler in an amount of 4 tons/hour, and the temperature of the 70th plate was adjusted to 112° C. The concentration of carbon tetrachloride in the purified EDC contained from the column bottom was 3,200 p.p.m. after 6 hours from the starting of the operation and increased to 3,700 p.p.m. after 3 days, but thereafter did not increase.

The temperature of the 70th plate was then lowered by 2° C., and the operation was continued. After 3 days, the concentration of carbon tetrachloride increased to 7,800 p.p.m., and thereafter did not increase. The maximum concentration of other low-boiling compounds during this operation was 150 p.p.m. and the change in its concentration was slight.

EXAMPLE 2

By employing the same crude EDC and distillation column as those employed in Example 1, 22.5 tons/hour of a mixed EDC containing the oxy-EDC, the direct-EDC and the uncracked-EDC in a molar ratio of 12.5:5:5 was fed to the 60th plate from the bottom of the column, and 37.5 tons/hour of a mixed EDC containing the oxy-EDC, the direct-EDC and the uncracked-EDC in a molar ratio of 2.5:10:25 was fed to the 30th plate from the bottom of the column. Steam was supplied to the reboiler in an amount of 6.5 tons/hour. The concentration of carbon tetrachloride in the purified EDC obtained from the column bottom increased to 3,050 p.p.m. after 6 hours and 3,500 p.p.m. after 3 days. The maximum concentration of other low-boiling compounds in the purified EDC during this operation was 200 p.p.m. and the change in its concentration was slight.

What we claim is:

1. In a method for purifying, 1,2-dichloroethane by passing through a distillation column a crude 1,2-dichloroethane produced by oxychlorination of ethylene with at least one of a crude 1,2-dichloroethane produced by direct chlorination of ethylene and a crude uncracked 1,2-dichloroethane recovered in thermal cracking of 1,2-dichloroethane, the improvement which comprises feeding a crude, 1,2-dichloroethane produced by the oxychlorination to an upper plate of a distillation column, feeding to a plate sufficiently below said upper plate at least one crude 1,2-dichloroethane of a crude 1,2-dichloroethane produced by the direct chlorination and a crude uncracked 1,2-dichloroethane recovered in thermal cracking, and recovering 1,2-dichloroethane as a bottom product having a substantially non-varying concentration of carbon tetrachloride over a time duration of said method sufficient to catalyze a thermal cracking of dichloroethane.

2. The method of claim 1, wherein the crude 1,2-dichloroethane fed to the upper plate further contains as a minor component at least one of a crude 1,2-dichloroethane produced by the direct chlorination and a crude uncracked 1,2-dichloroethane recovered in the thermal cracking.

3. The method of claim 1, wherein said at least one crude 1,2-dichloroethane further contains as a minor component a crude 1,2-dichloroethane produced by the oxychlorination.

4. The method of claim 1, wherein carbon tetrachloride included in the crude 1,2-dichloroethane fed is recovered together with 1,2-dichloroethane as a bottom product, while other compounds having a lower boiling point than carbon tetrachloride are removed as a distillate.

* * * * *